US006838121B2

(12) United States Patent
Weimer

(10) Patent No.: US 6,838,121 B2
(45) Date of Patent: Jan. 4, 2005

(54) SYSTEM AND METHOD FOR CONTROLLING DEPOSITION PARAMETERS IN PRODUCING A SURFACE TO TUNE THE SURFACE'S PLASMON RESONANCE WAVELENGTH

(75) Inventor: Wayne A. Weimer, Plano, TX (US)

(73) Assignee: Zyvex Corporation, Richardson, TX (US)

( * ) Notice: Subject to any disclaimer, the term of this patent is extended or adjusted under 35 U.S.C. 154(b) by 615 days.

(21) Appl. No.: 09/852,992

(22) Filed: May 10, 2001

(65) Prior Publication Data

US 2003/0026900 A1 Feb. 6, 2003

(51) Int. Cl.[7] ............................................... C23C 14/14

(52) U.S. Cl. .................... 427/250; 427/596; 204/192.26

(58) Field of Search .............................. 427/250, 596; 204/192.26

(56) References Cited

U.S. PATENT DOCUMENTS

| | | | |
|---|---|---|---|
| 5,567,628 A | 10/1996 | Tarcha et al. ................ | 436/525 |
| 5,609,907 A | 3/1997 | Natan .......................... | 427/2.12 |
| 5,846,610 A | * 12/1998 | Sunderland ................... | 427/534 |
| 5,939,021 A | 8/1999 | Krauledal et al. | |
| 5,991,488 A | 11/1999 | Tollin et al. | |
| 6,025,202 A | 2/2000 | Natan | |
| 6,608,716 B1 | 8/2003 | Armstrong et al. | |

FOREIGN PATENT DOCUMENTS

| | | | |
|---|---|---|---|
| EP | 646660 A1 * | 4/1995 | ........... C23C/14/48 |
| WO | WO 98/04902 | 2/1998 | |

OTHER PUBLICATIONS

Schelgel et al., Anal. Chem. (1991) 63, pp. 241–247.*
Sennett, R. S. et al., "The Structure of Evaporated Metal Films and Their Optical Properties," Journal of the Optical Society of America, vol. 40, No. 4, Apr. 1950, pp. 203–211.
Schlegel et al., "Silver–Island Films as Substrates for Enhanced Raman Scattering: Effect of Deposition Rate on Intensity", Anal. Chemistry, 1991, vol. 63, pp. 241–247.
Van Duyne, et al., "Atomic Force Microscopy and Surface–Enhanced Raman Spectroscopy I Ag Island Films and Ag Film Over Polymer Nanosphere Surfaces Supported on Glass," J. Phys. Chem., vol. 99(3), Aug. 1, 1993, pp. 2101–2115.
Levlin et al., "Evaporaton of Gold Thin Films on Mica: Effect of Evaporation Parameters", Applied Surface Science, vol. 115, 1997, pp. 31–38.
Hulteen et al., "Nanosphere Lithography: Size–Tunable Silver Nanoparticle and Surface Cluster Arrays", J. Phys. Chem B 1999, vol. 103, pp. 3854–3863.

Jensen et al., "Nanosphere Lithography: Surface Plasmon Resonance Spectrum of a Periodic Array of Silver Nanoparticles by Ultraviolet—Visible Extinction Spectroscopy and Electrodynamic Modeling", J. Phys. Chem. B 1999, vol. 103, pp. 2394–2401.
Jensen et al., "Nanosphere Lithography: Effect of the External Dielectric Medium on the Surface Plasmon Resonance Spectrum of a Periodic Array of Silver Nanoparticles", J. Phys. Chem. B, 1999, vol. 103, pp. 9846–9853.
Link et al., "Shape and Size Dependence of Radiative, Non–Radiative and Photothermal Properties of Gold Nanocrystals", Int Reviews in Physical Chemistry, 2000, vol. 19, No. 3, pp. 409–453.
Haynes et al., "Nanosphere Lithography: A Versatile Nanofabrication Tool for Studies of Size–Dependent Nanoparticle Optics,", J. Phys. Chem. B, 2001, vol. 105, pp. 5599–5611.
Malinsky et al., "Nanosphere Lithography: Effect of Substrate on the Localized Surface Plasmon Resonance Spectrum of Silver Nanoparticles", J. Phys. Chem. B, 2001, vol. 105, pp. 2343–2350.
Malinsky et al., "Chain Length Dependence and Sensing Capabilities of the Localized Surface Plasmon Resonance of Silver Nanoparticles Chemically Modified with Alkanethiol Self–Assembled Monolayers", J. Am. Chem. Soc., 2001, vol. 123, pp. 1471–1482.
Levlin et al., "Evaporation of Silver Thin Films on Mica," Applied Surface Science vol. 171, 2001, pp. 257–264.
Nanosphere Lithography: tunable Localized Surface Plasmon Resonance Spectra of Silver Nanoparticles by Traci R. Jensen et al., Dept. of Chemistry, Northwestern University, Evanston, IL, Published on Web Oct. 21, 2000.
Surface–Enhanced Raman Scattering by Alan Campion et al., Chemical Society Reviews, 1998, vol. 27.
Raman Spectroscopy by Shawn P. Mulvaney et al., Analytical Chemistry, vol. 72, No. 12, Jun. 15, 2000.

(List continued on next page.)

Primary Examiner—Timothy Meeks
(74) Attorney, Agent, or Firm—Haynes and Boone, LLP

(57) ABSTRACT

A system and method are disclosed which enable deposition parameters to be controlled in producing a metal surface to tune the localized surface plasmon resonance (LSPR) wavelength of such metal surface to a desired wavelength. For example, the surface produced may be used as an enhancement surface within a surface-enhanced spectroscopy process, wherein such surface is produced having a LSPR wavelength that provides the maximum extinction of a particular excitation light. In one embodiment, a metal is deposited onto a substrate, while controlling one or more deposition parameters to tailor the LSPR of the resulting metal surface to a desired wavelength. In one embodiment, the substrate is smooth, and does not require a mask prearranged thereon for controlling the LSPR wavelength. Rather, deposition parameters, such as temperature of the substrate, deposition rate, and film thickness may be controlled to effectively tune the LSPR wavelength of the metal surface.

43 Claims, 6 Drawing Sheets

OTHER PUBLICATIONS

Thin films by Regular Patterns of Metal Nanoparticles: Tailoring the Optical Properties by Nanodesign by W. Gotschy et al., Applied Physics B, Spring 1996.

Kim, W., et al., "Fractals in Microcavities: Giant Coupled, Multiplicative Enhancement of Optical Responses", Physical Review Letters, vol. 82, Issue 24, Jun. 14, 1999, pp. 4811–4814.

Kneipp, Katrin, et al, "Single Molecule Detection Using Surface–Enhanced Raman Scattering (SERS)", Physical Review Letters, vol. 78, No. 9, Mar. 3, 1997, pp. 1667–1670.

Nie, Shuming, et al., "Probing Single Molecules and Single Nanoparticles by Surface–Enhanced Raman Scattering", Science, vol. 275, Feb. 21, 1997, pp. 1102–1106.

* cited by examiner

SYSTEM AND METHOD FOR CONTROLLING DEPOSITION PARAMETERS IN PRODUCING A SURFACE TO TUNE THE SURFACE'S PLASMON RESONANCE WAVELENGTH

TECHNICAL FIELD

This invention relates in general to producing surfaces having a localized surface plasmon resonance wavelength tuned to a desired value. More specifically, the present invention relates to a system and method for controlling deposition parameters to produce an atomically roughened surface having a localized surface plasmon resonance wavelength that is tuned to a desired value. For example, such localized surface plasmon resonance wavelength may be tuned to provide maximum extinction of a particular excitation light source to enable such surface to act as an enhancement surface that provides optimum enhancement in a surface-enhanced spectroscopy process, such as surface-enhanced Raman spectroscopy.

BACKGROUND

Nanotechnology is becoming a quickly advancing field. For instance, extraordinary advances are being made in nanometer-scale electronics and mechanics, including handling and assembly of nanometer-scale components. For instance, suggestions are beginning to be made as to designs for molecular-scale or atomic-scale devices. Someday devices may be assembled on the molecular or even atomic scales, e.g., providing precision in such devices at the molecular or atomic levels. As design and/or analysis continues to progress on such a small scale, suitable analytical techniques for properly identifying and/or analyzing such small-scale building blocks as molecules or atoms, as well as their interaction, become increasingly important.

Various techniques have been developed in the prior art to aid in recognizing/analyzing molecular arrangements. For instance, spectroscopy is a well-known analytical technique concerned with the measurement of the interaction of radiant energy with matter and with the interpretation of such interaction. Interpretation of the spectra produced by various spectroscopic instrumentation has been used to provide fundamental information on atomic and molecular energy levels, the distribution of species within those levels, the nature of processes involving change from one level to another, molecular geometries, chemical bonding, and interaction of molecules in solution, as examples.

One type of spectroscopy is known as vibrational spectroscopy. Vibrational spectroscopy provides a relatively useful technique for characterizing molecules and for determining their chemical structure. The vibrational spectrum of a molecule, based on the molecular structure of that molecule, is a series of distinguishable lines which constitutes a unique fingerprint of that specific molecular structure. Optical fibers may be used to measure the vibrational spectrum by an optical absorption process, wherein optical energy from a source is delivered to a sample via one fiber, and after passage through the sample, an optical signal generated by the exciting optical energy is collected by the same or, more preferably, another fiber. The collected light may be directed to a monochrometer/or a photodetector for analyzing its wavelength and/or intensity.

For many years, it has been known that when certain molecules are illuminated by a beam of light, for example ultraviolet, visible, or near infrared, a small fraction of the incident photons are retained momentarily by some of the molecules, causing a transition of the electrons within the energy levels of some of those molecules to higher vibrational levels of the ground electronic state. Often, these are elastic collisions, and the molecules return to their original vibrational level by releasing photons. Photons are emitted in all directions at the same wavelength as the incident beam (i.e., they are scattered). This is commonly known as "Rayleigh scattering."

Another important type of spectroscopy is known as "Raman spectroscopy," which is a process that makes use of "Raman scattering" to investigate molecular vibrations and rotations. "Raman scattering" is generally defined as the scattering of light by molecules in which there is a change of frequency due to the molecules gaining or losing energy as a result of transitions between vibrational or rotational energy levels. The phenomenon was discovered in 1928 by C. V. Raman. More specifically, Raman discovered that when certain molecules are illuminated, a small percentage of the molecules which have retained a photon, drop to a different vibrational level of the ground electronic state. The radiation emitted from these molecules will therefore be at a different energy and hence a different wavelength. If the molecule drops to a higher vibrational level of the ground electronic state, the photon emitted is at a lower energy or longer wavelength than that absorbed. This is commonly referred to as "Stokes-shifted Raman scattering." If a molecule is already at a higher vibrational state before it absorbs a photon, it can impart this extra energy to the remitted photon thereby returning to the ground state. In this case, the radiation emitted is of higher energy (and shorter wavelength) and is commonly referred to as "anti-Stokes-shifted Raman scattering." In a set of molecules under normal conditions, the number of molecules at ground state is generally much greater than those at an excited state. Therefore, the odds of an incident photon interacting with an excited molecule and being scattered with more energy than it carried upon collision is typically very small. Thus, when a set of molecules are under study, photon scattering at frequencies higher than that of the incident photons (anti-Stokes frequencies) is typically minor relative to that at frequencies lower than that of the incident photons (Stokes frequencies). Consequently, the Stokes frequencies are usually analyzed in Raman spectroscopy processes of the prior art.

The amount of energy lost to, or gained from, a molecule in this way is quantized, resulting in the scattered photons having discrete wavelength shifts. These wavelength shifts can be measured by a spectrometer. Raman scattering was initially considered to have the potential to be useful as an analytical tool to identify certain molecules, and as a means of studying molecular structure. However, interest in Raman scattering faded somewhat as other methods, such as infrared spectroscopy, gained popularity.

Interest in Raman spectroscopy was renewed with the advent of the laser as a light source. Its intense coherent light overcame some of the sensitivity drawbacks initially encountered in Raman spectroscopy. Moreover, it was discovered that when the wavelength of the incident light is at or near the maximum absorption frequency of the molecule, and hence can cause electronic as well as vibrational transitions in the molecules, resonance Raman scattering is observed. With resonance Raman scattering, the re-emitted photons still show the differences in vibrational energy associated with Raman scattering. However, with resonance Raman scattering, the electronic vibrational absorption is approximately 1000 times more efficient. Even with the increased signal from resonance Raman scattering, its usefulness as an analytic tool was limited due to its still comparatively weak signal.

Interest in Raman spectroscopy further increased when, in 1974, M. Fleischmann et al. discovered surface-enhanced Raman spectroscopy (SERS), though did not recognize it as such. See M. Fleischmann, P. J. Hendra, and A. J. McQuillan, Chem. Phys. Lett., 1974, 26, 163. Specifically, Fleischmann et al. observed intense Raman scattering from pyridine adsorbed onto a roughened silver electrode surface from aqueous solution. Fleischmann's approach was to roughen the electrode to increase its surface area and, hence, the number of adsorbed molecules available for study. Dr. Richard P. Van Duyne et al. later recognized that the large intensities observed could not be accounted for simply by the increase in the number of scatterers present and proposed that an enhancement of the scattered intensity occurred in the adsorbed state. See D. L. Jeanmaire and R. P. Van Duyne, J. Electroanal Chem., 1977, 84, 1. Also in 1977 Creighton et al. recognized that the increased Raman signal was not possible by more scatterers alone and proposed an enhancement mechanism. See M. G. Albrecht and J. A. Creighton, J. Am. Chem. Soc. 99, 5215 (1977). Thus, it was recognized that Raman scattering efficiency can be enhanced when a compound is adsorbed on or near special metal surfaces. That is, a significant increase in the intensity of Raman light scattering can be observed when molecules are brought into close proximity to (but not necessarily in contact with) certain metal surfaces that are atomically "roughened." Metal colloids also demonstrate such signal enhancement effect. Such phenomenon is referred to as "surface-enhanced Raman scattering" (SERS), and use of such surface-enhancement has enabled enhancements in Raman scattering efficiency by factors of $10^6$ to be observed.

The cause of the SERS effect is not completely understood. However, at least two separate factors contributing to SERS have been advanced in the prior art. First, the metal surface contains minute irregularities. These irregularities may be thought of as spheres (in a colloid, they are spheroidal or nearly so). Those particles with diameters of approximately 1/10th the wavelength of the incident light have been thought to contribute most to the effect. The incident photons induce a field across the particles which, being metal, have very mobile electrons.

In certain configurations of metal surfaces or particles, groups of surface electrons can be made to oscillate in a collective fashion in response to an applied oscillating electromagnetic field. Such a group of collectively oscillating electrons is called a "plasmon." The incident photons supply this oscillating electromagnetic field. The induction of an oscillating dipole moment in a molecule by incident light is the source of the Raman scattering. The effect of the resonant oscillation of the surface plasmons is to cause a large increase in the electromagnetic field strength in the vicinity of the metal surface. This results in an enhancement of the oscillating dipole induced in the scattering molecule and hence increases the intensity of the Raman scattered light. The effect is to increase the apparent intensity of the incident light in the vicinity of the particles.

A second factor considered to contribute to the SERS effect is molecular imaging. A molecule with a dipole moment, which is in close proximity to a metallic surface, will induce an image of itself on that surface of opposite polarity (i.e., a "shadow" dipole on the plasmon). The proximity of that image is thought to enhance the power of the molecules to scatter light. Put another way, this coupling of a molecule having an induced or distorted dipole moment to the surface plasmons greatly enhances the excitation probability. The result is a very large increase in the efficiency of Raman light scattered by the surface-absorbed molecules.

The SERS effect can be enhanced through combination with the resonance Raman effect. When an excitation light source (e.g., laser) used to excite SERS is in resonance with an electronic transition of the substance, such condition is referred to as surface-enhanced resonance Raman scattering (or "SERRS" or "resonant SERS"). As described above, an enhancement in the efficiency of Raman scattering on the order of $10^6$ fold has been observed with SERS. An additional $10^3$ fold enhancement in the efficiency of Raman scattering has been observed with SERRS.

Accordingly surface-enhanced Raman spectroscopy (both SERS and SERRS) are capable of providing great information for use in identifying and analyzing molecules. Accordingly surface-enhanced Raman spectroscopy is being used in a variety of applications, including detection of molecules and analysis of molecular structure, as examples.

SUMMARY OF THE INVENTION

The present invention is directed to a system and method which enable deposition parameters to be controlled in producing a surface to tune the plasmon resonance wavelength of such surface to a desired wavelength. For example, the surface being produced may be intended as an enhancement surface for use in a surface-enhanced spectroscopy process (such as surface-enhanced Raman spectroscopy), and various embodiments of the present invention enable such surface to be produced with a plasmon resonance wavelength that provides the maximum extinction of a particular excitation light (e.g., laser) to be used in the spectroscopy process, thereby enabling the surface to provide optimum enhancement within the spectroscopy process.

According to at least one embodiment of the present invention, a method and system are disclosed for producing a metal surface that has a desired localized surface plasmon resonance (LSPR) wavelength. Such metal surface is produced by depositing metal onto a substrate, while controlling one or more deposition parameters to tailor the LSPR of the resulting metal surface to a desired wavelength. According to at least one embodiment, the substrate is a clean, smooth substrate, and does not require a mask prearranged thereon for controlling the LSPR wavelength. Rather, deposition parameters, such as temperature of the substrate, deposition rate, and film thickness (or deposition amount) may be controlled to effectively tune the LSPR wavelength of the resulting metal surface.

An example of the desired wavelength to which the LSPR may be tuned includes a wavelength that provides maximum extinction of a particular excitation light source. Accordingly, a metal surface may be produced having a LSPR wavelength that is effectively tuned to provide maximum extinction of a particular excitation light source (e.g., a laser) used in a surface-enhanced spectroscopy process, and therefore such surface may provide an optimum surface for use as an enhancement surface within such spectroscopy process. Thus, for instance, according to at least one embodiment, a method and system are disclosed for producing an enhancement surface for use in a surface-enhanced spectroscopy process, wherein such enhancement surface has a desired LSPR wavelength (e.g., a LSPR wavelength that provides maximum extinction of a particular excitation light source utilized in the spectroscopy process). More specifically, the wavelength of an excitation light source used in the surface-enhanced spectroscopy process may be determined, and then according to at least one embodiment of the present invention an appropriate value for one or more deposition parameters to be used in depositing metal onto a substrate to produce an enhancement surface having a LSPR wavelength that provides optimum enhancement for the excitation light source may be determined. Such appropriate value may be determined in certain embodiments through use of a processor-based device, which may be executing a control algorithm thereon to specify appropriate value(s) of deposition parameters of a particular deposition process that yield a metal surface having the LSPR wavelength that provides optimum enhancement of the excitation light source. Such determined value for the deposition parameters may then be utilized in a deposition process for depositing metal onto a substrate to produce an enhancement surface having the LSPR wavelength that provides optimum enhancement for the excitation light source.

Additionally, various embodiments of the present invention enable a control algorithm to be derived for controlling a deposition process in a manner that results in such deposition process producing a metal film that has a LSPR of a desired wavelength. For instance, a particular deposition process (e.g., a thermal evaporation process) may first be analyzed. More specifically, such deposition process may be utilized to deposit metal samples onto one or more substrates, wherein the value of at least one deposition parameter is varied for each of the metal samples deposited. Thus, various samples may be obtained with each sample produced according to different deposition parameter values. The metal samples obtained may then be analyzed to determine the effect of the deposition parameter(s) on the LSPR wavelength of such metal samples. Based on such analysis, a control algorithm may be determined that defines a resulting LSPR wavelength of a metal film produced by the deposition process under study as a function of the deposition parameter(s). Accordingly, from such derived control algorithm for the particular deposition process, one or more appropriate values of deposition parameter(s) that result in production of a metal film having a LSPR of a desired wavelength are determinable.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION

Figure 1:
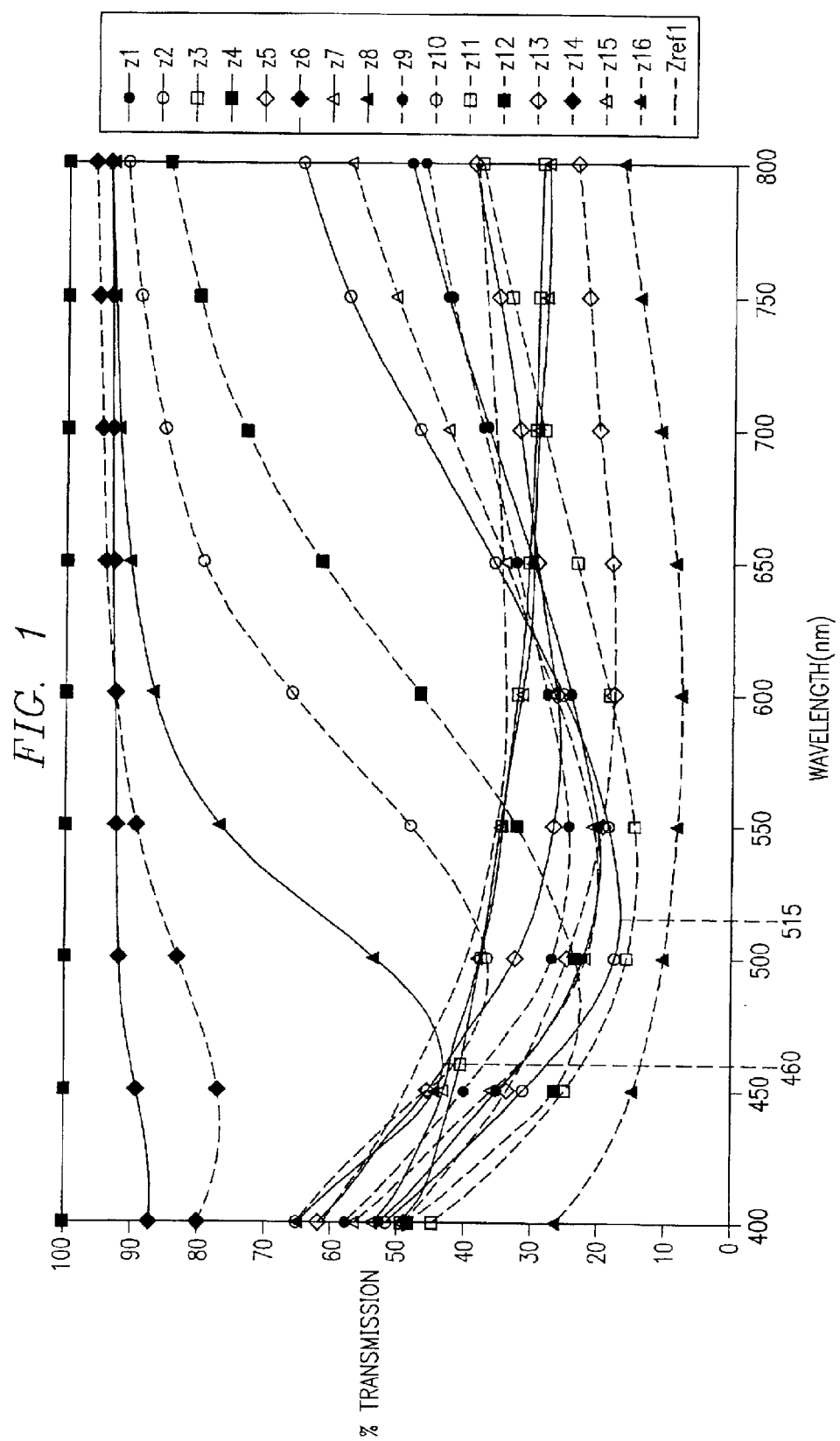
FIG. 1 shows a plot illustrating the amount of radiant transmission detected through various enhancement surfaces that may be produced according to various embodiments of the present invention.

Metal surfaces exhibit an optical property known as "localized surface plasmon resonance" (LSPR). When metal surfaces are excited by electromagnetic radiation, they exhibit collective oscillations of their conduction electrons, known as localized surface plasmons. A "plasmon" is a collection of electrons that oscillate at a certain frequency. The localized surface plasmons may couple into the frequency of an incident radiation. For instance, in a surface-enhanced spectroscopy process (e.g., SERS), the excitation light incident on the enhancement surface may couple into the enhancement surface and then into the molecule(s) adsorbed on such surface.

Various situations may arise in which it is desirable to produce a surface in a manner such that its LSPR is tuned to a particular wavelength. Thus, a desire exists for a system and method for producing a surface, which enable the surface to be produced having its LSPR tuned to a desired wavelength. One situation in which it may be desirable to produce a surface having its LSPR tuned to a particular wavelength is when producing an enhancement surface for use in surface-enhanced spectroscopy. For instance, as described in greater detail hereafter, maximizing the amount of the excitation light that is absorbed by an enhancement surface optimizes the enhancement provided by such surface in spectroscopy processes (such as SERS). That is, utilizing an enhancement surface in a spectroscopy process (such as SERS), which comprises an LSPR having a wavelength corresponding to the extinction maximum ($\lambda_{max}$) for an applied excitation light, may provide the optimum enhancement of molecule(s) adsorbed thereon. Of course, other situations may also arise in which it is desirable to produce a surface having its LSPR controllably tuned to a particular wavelength, and any such situation is intended to be within the scope of the present invention.

By varying characteristics of the surface, the LSPR wavelength of such surface may be varied. More specifically, by varying the surface's "roughness" (on the atomic scale), its LSPR wavelength may be varied. Various embodiments of the present invention enable the roughness of a surface to be effectively controlled during production of such surface in a manner to accurately tune the surface's LSPR to a desired wavelength. Thus, for example, an enhancement surface can be produced such that its LSPR can be effectively "tuned" to a wavelength corresponding to the extinction maximum ($\lambda_{max}$) for a given excitation light source, which may enable the spectroscopy process (e.g., SERS) in which such enhancement surface is utilized to be optimized. As described further hereafter, various embodiments of the present invention provide a method for accurately tuning the LSPR of an enhancement surface to provide optimum enhancement for a given excitation light source. More specifically, various embodiments provide a method for producing an enhancement surface having a LSPR that is tailored to provide optimum enhancement for an excitation light source having a particular wavelength. For instance, certain embodiments control deposition characteristics (e.g., deposition rate, temperature, and film thickness) to produce an enhancement surface having a LSPR with a wavelength that corresponds to the extinction maximum ($\lambda_{max}$) for a given excitation light source. While various examples are described herein for producing an "enhancement surface" that may be used in a surface-enhanced spectroscopy process, such as surface-enhanced Raman spectroscopy, it should be understood that the present invention is not intended to be limited to such enhancement surfaces, but is instead intended to encompass any type of surface for which a particular LSPR wavelength may be desired. Thus, enhancement surfaces described herein are intended solely as examples, which render the disclosure enabling for production of many other types of surfaces which may or may not be used in a surface-enhanced spectroscopy process.

Various embodiments of the present invention utilize a deposition method having particular deposition parameters (e.g., particular deposition rate, temperature, and film thickness) to produce an enhancement surface having a particular LSPR wavelength. According to a preferred embodiment, a desired surface is produced by depositing the material for forming such surface (e.g., silver or other suitable metal) onto a clean, smooth substrate (such as glass, metal, dielectric surface, or any other smooth substrate surface). According to one implementation, a smooth microscope cover slip is utilized as such a substrate. The substrate is preferably sufficiently smooth so as to not significantly alter the roughness of the surface produced by the deposition process (e.g., so that the substrate does not impart roughness to the surface deposited hereon). Most preferably, thermal evaporation is utilized to deposit the metal onto the substrate. Alternatively, any suitable deposition technique may be utilized, including sputter deposition techniques, electron-beam lithography, laser ablation, and chemical vapor deposition (CVD), as examples. In a preferred embodiment, the metal may be deposited directly onto the substrate, without requiring a mask to be first arranged on the substrate. Various embodiments of the present invention enable certain deposition parameters, such as the substrate temperature, deposition rate, and amount of metal to deposit) to be controlled in a manner to accurately tune the LSPR of the resulting surface to a desired wavelength. Thus, in various embodiments, the LSPR of the resulting surface may be tuned through control of the deposition parameters, rather than utilizing a mask arranged on the substrate to attempt to control the surface's LSPR. Because use of a mask is not required in various embodiments of the present invention, a relatively simple production technique is provided. The relative simplicity of the production technique of various embodiments may enable great control of a surface's LSPR through controlling deposition parameters, without requiring that user's have the ability to perform relatively complex lithographic processes or other relatively complex production steps. For instance, thermal evaporators are becoming increasingly common as lab equipment, and because certain embodiments enable the LSPR of a surface to be tailored through controlling deposition parameters when depositing a metal onto a substrate using a thermal evaporator, such production technique may be a viable option for many users.

Turning to FIG. 1, a plot illustrating the amount of radiant transmission detected through various enhancement surfaces that may be produced according to embodiments of the present invention is shown. More specifically, the transmission percentage is plotted for 17 enhancement surfaces that were each produced according to different deposition parameters. For instance, each of the 17 enhancement surfaces were produced with one or more of the following deposition parameter values varied: deposition rate, substrate temperature during deposition, and deposition amount (e.g., film thickness). As the plot of FIG. 1 illustrates, minimum transmission for each surface, which corresponds to the maximum extinction (or maximum absorption of the excitation light into the surface), occurs at various wavelengths. That is, as the deposition parameters vary in producing the surfaces, the LSPR wavelengths of such surfaces vary.

Accordingly, each surface provides minimum transmission (and therefore maximum absorption) of different wavelengths of an excitation light applied thereto. For instance, surface "Z2" produced according to a first set of deposition parameters has minimum transmission of an excitation light having a wavelength of 515 nanometers (nm), while surface "Z8" produced according to a second set of deposition parameters has a minimum transmission of an excitation light having a wavelength of 460 nm. As described in greater detail hereafter, various embodiments enable deposition parameters to be intelligently controlled to produce a surface having a LSPR wavelength tuned for maximum absorption (or maximum extinction) of a given excitation light source wavelength. For instance, assuming a user desires an optimum enhancement surface for use in performing SERS with an excitation light source having a wavelength of 460 nm, deposition parameters may be controlled to produce an enhancement surface, such as surface Z8 in the example of FIG. 1, that has a LSPR wavelength tuned for maximum absorption of such 460 nm excitation light source.

Figure 2:
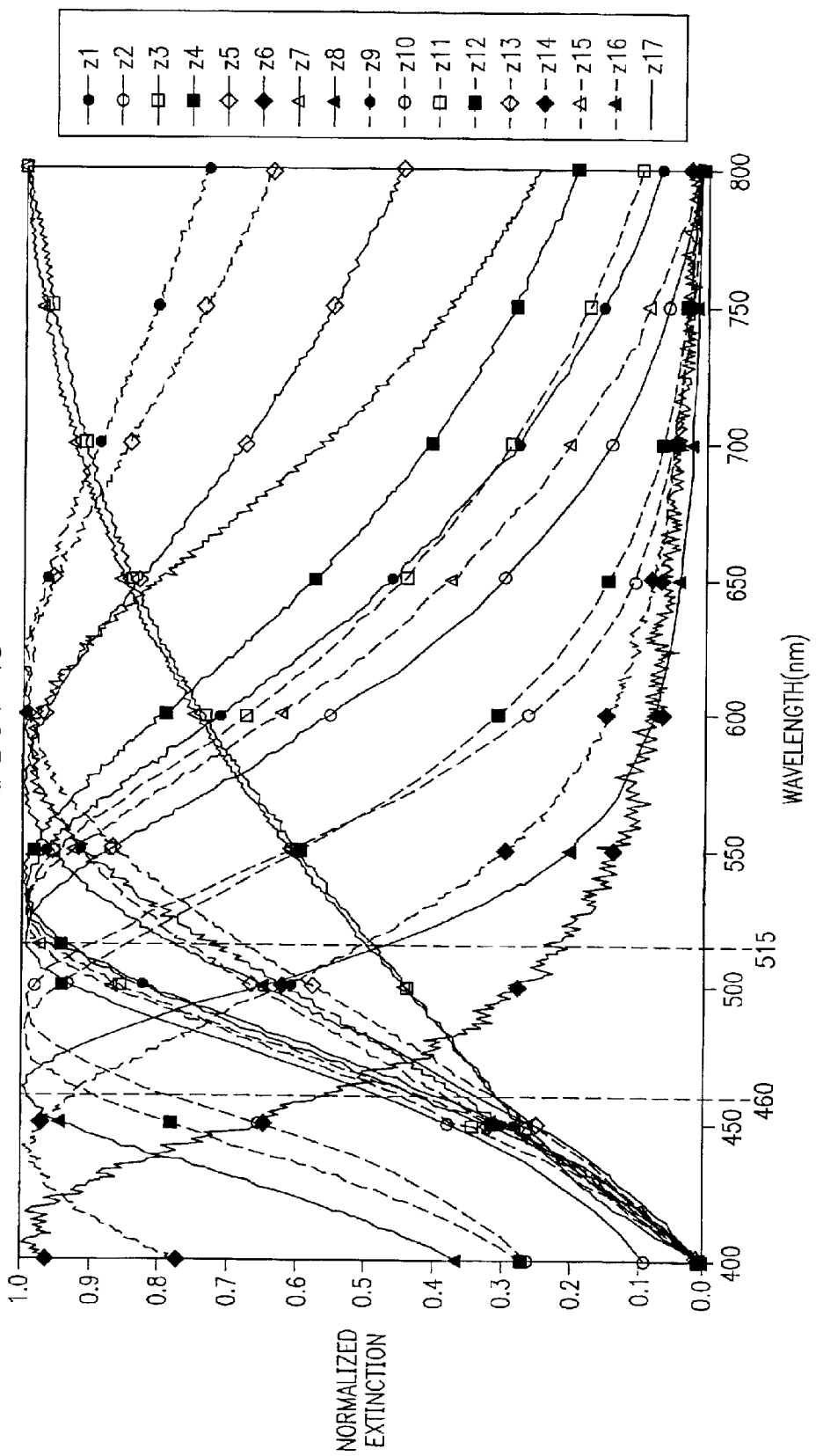
FIG. 2 shows the surface plots of FIG. 1 with the maximum extinction (or maximum absorption) of each enhancement surface normalized to 1.0 and the minimum extinction is of each enhancement surface normalized to 0.0.

FIG. 2 normalizes the surface plots of FIG. 1 such that the maximum extinction (or maximum absorption) of each enhancement surface is mapped to 1.0 and the minimum extinction is of each enhancement surface is mapped to 0.0. That is, the minimum transmission values of FIG. 1 are mapped to value 1.0 in FIG. 2. Again, the example of FIG. 2 shows that enhancement surface Z8 has a LSPR that provides maximum extinction at 460 nm, and enhancement surface Z2 has a LSPR that provides maximum extinction at 515 nm. As the example of FIGS. 1 and 2 illustrate, the maximum extinction LSPR wavelength of the different enhancement surfaces occurs at various points throughout the excitation wavelengths 400 nm through 800 $\mu$m. Thus, according to various embodiments of the present invention, deposition parameters may be controllably varied to produce an enhancement surface having a LSPR with an extinction wavelength tailored to any desired point within the visible (i.e., 400–700 nm) and nearby parts of the infrared and ultraviolet spectra. Accordingly, an enhancement surface can be produced having a LSPR that is tailored to provide the maximum extinction of an excitation light source having a given wavelength within such spectra. Additionally, it should be understood that the present invention is not intended to be limited solely to the 17 exemplary surfaces plotted in FIGS. 1 and 2, but rather various other surfaces may be produced according to various embodiments of the present invention, wherein the deposition parameters in producing such other surfaces may be controlled to result in a LSPR of any desired wavelength.

Various embodiments of the present invention provide a method for intelligently controlling deposition parameters in a manner to produce an enhancement surface having a LSPR of a desired wavelength. Thus, if a spectroscopist utilizes an excitation light source (e.g., laser) of a given wavelength (e.g., 460 nm) in a surface-enhanced spectroscopy process (e.g., SERS or SERRS), an enhancement surface may be produced having a LSPR that is tailored to such excitation light source wavelength. That is, an enhancement surface may be produced having a LSPR wavelength that provides the maximum extinction of the excitation light source, thereby optimizing the enhancement provided by such surface. Thus, various embodiments enable an enhancement surface (e.g., a metal film) to be deposited on a substrate in accordance with one or more controlled parameters to produce an enhancement surface with a desired LSPR wavelength.

Figures 3A, 3B, 3C:
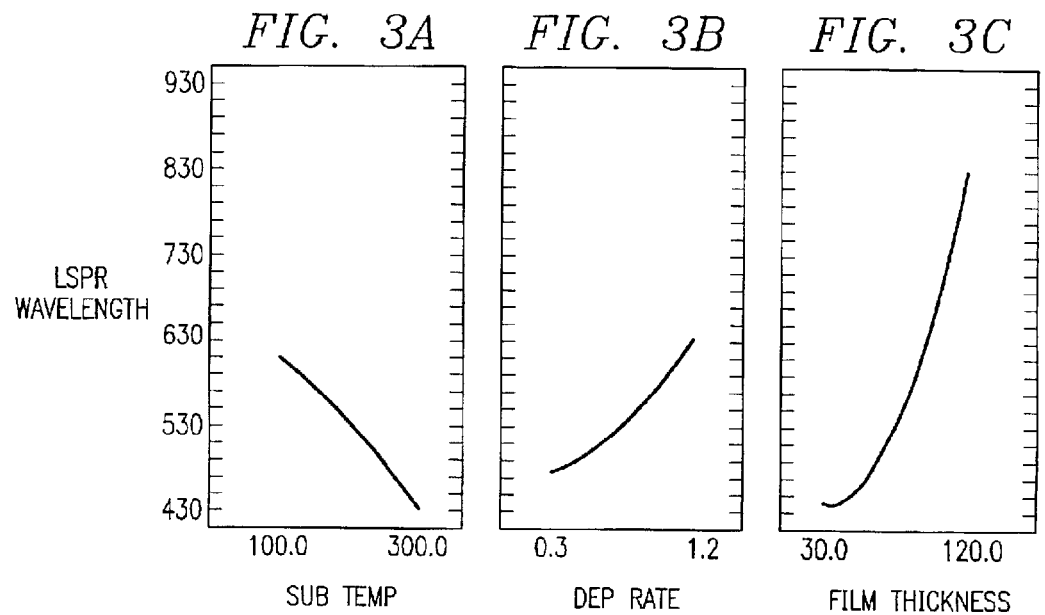
FIGS. 3A–3C show plots illustrating the effects of controllable deposition parameters of a preferred embodiment on the plasmon wavelength of a resulting enhancement surface.

While various deposition parameters may be controlled in various embodiments of the present invention in order to produce a desired enhancement surface, in a preferred embodiment one or more of the following deposition parameters are controlled: deposition rate, substrate temperature during deposition, and deposition amount (to control film thickness). Turning to FIGS. 3A–3C, exemplary plots are shown which illustrate the effects of such deposition parameters on the LSPR wavelength of the resulting enhancement surface of one implementation of a preferred embodiment. More specifically, such plots may be derived through analysis of samples of metal surfaces produced by a particular deposition process (such as the exemplary 17 surfaces of FIGS. 1 and 2). In the example of FIG. 3A, the effect that substrate temperature during deposition has on the resulting LSPR wavelength of a metal surface is shown. As shown in the example of FIG. 3A, substrate temperature during deposition is varied from 100° Celsius (C.) to 300° C., while the deposition rate and film thickness parameters are held constant. Thus, the substrate temperature during deposition is one deposition parameter that may be controllably varied to effect the LSPR wavelength of the resulting enhancement surface. FIG. 3A illustrates that as the substrate temperature increases within the particular deposition process under study (e.g., a particular thermal evaporation process for depositing a silver film onto a substrate), it generally results in a decrease in the LSPR wavelength of the resulting enhancement surface. For instance, in the example of FIG. 3A, as the substrate temperature during deposition increases from 100° C. to 300° C., the LSPR wavelength of the resulting enhancement surface decreases from approximately 610 nm to approximately 430 nm.

In the example of FIG. 3B, the effect that deposition rate has on the resulting LSPR wavelength of a metal surface is shown. As shown in the example of FIG. 3B, deposition rate is varied from 0.3 Angstroms per second (Å/s) to 1.2 Å/s, while the substrate temperature during deposition and film thickness parameters are held constant. Thus, the deposition rate is a deposition parameter that may be controllably varied to effect the LSPR wavelength of the resulting enhancement surface. FIG. 3B illustrates that as the deposition rate increases within the particular deposition process under study, it generally results in an increase in the LSPR wavelength of the resulting enhancement surface. For instance, in the example of FIG. 3B, as the deposition rate increases from 0.3 Å/s to 1.2 Å/s, the LSPR wavelength of the resulting enhancement surface increases from approximately 490 nm to approximately 650 nm.

In the example of FIG. 3C, the effect that film thickness has on the resulting LSPR wavelength of a metal surface is shown. As shown in the example of FIG. 3C, film thickness is varied from 30 Å to 120 Å, while the substrate temperature during deposition and deposition rate parameters are held constant. Thus, the film thickness is a deposition parameter that may be controllably varied to effect the LSPR wavelength of the resulting enhancement surface. FIG. 3C illustrates that as the film thickness increases within the particular deposition process under study, it generally results in an increase in the LSPR wavelength of the resulting enhancement surface. For instance, in the example of FIG. 3C, as the film thickness increases from 30 Å to 120 Å, the LSPR wavelength of the resulting enhancement surface increases from approximately 450 nm to approximately 830 nm.

Thus, FIGS. 3A–3C illustrate the sensitivity of the LSPR wavelength of a resulting surface to variances in a particular deposition parameter. For instance, in the example of FIG. 3A, the effect that substrate temperature has on the resulting LSPR wavelength is relatively gradual. That is, a small variance in substrate temperature for a given deposition rate and film thickness results in a relatively small effect on the resulting LSPR wavelength. In the example of FIG. 3B, the effect that deposition rate has on the resulting LSPR wavelength is also relatively gradual. That is, a small variance in deposition rate for a given substrate temperature and film thickness results in a relatively small effect on the resulting LSPR wavelength. In the example of FIG. 3C, the effect that variances in film thickness has on the resulting LSPR wavelength is much greater than substrate temperature and deposition rate. That is, a small variance in film thickness for a given substrate temperature and deposition rate results in a relatively large effect on the resulting LSPR wavelength. Again, such effects of deposition parameters may differ in other deposition processes. However, regardless of the deposition process being utilized, a similar analysis of samples produced according to varying deposition parameters may be performed to determine the effect that each deposition parameter of the particular process has on the resulting LSPR wavelength. From the analysis of the exemplary deposition process under study in FIGS. 3A–3C, it can be determined that great control of film thickness may be necessary to achieve a desired LSPR wavelength, while less control of substrate temperature and deposition rate may be necessary (as a small variance in those parameters does not result in as great of effect on the resulting LSPR wavelength as with film thickness).

It should be understood that FIGS. 3A–3C illustrate the effect that each deposition parameter have on the resulting LSPR wavelength of a metal surface produced by an exemplary deposition process, and various other deposition processes may yield different results. That is, the example provided in FIGS. 3A–3C illustrate how variances in substrate temperature during deposition, deposition rate, and film thickness effect the LSPR wavelength of the resulting surface produced by a particular thermal evaporation process utilized to deposit silver onto a substrate. While different results may be achieved in various different deposition processes (including different types of thermal evaporation processes), the specific effects that deposition parameters have on LSPR wavelength in a particular deposition process may be analyzed to derive appropriate deposition parameter values for a particular deposition process under study that result in production of a metal surface having a desired LSPR wavelength in the manner described herein. Accordingly, while specific examples are provided herein as to how certain deposition parameters of a particular deposition process (e.g., a particular thermal evaporation process) may effect LSPR wavelength, the scope of the present invention is not intended to be limited solely to a deposition process that yields the specific results described herein, but rather any desired deposition process (which may yield different results) may be analyzed in a similar manner to determine appropriate deposition parameters that may be utilized to produce a surface having a desired LSPR wavelength in the manner described herein.

It appears that surface "roughness" may be a parameter that dictates the LSPR wavelength of a surface. That is, it appears that as the roughness of the produced surface increases, its LSPR wavelength increases. Such a conclusion is consistent with the results provided in FIGS. 3A–3C for a particular deposition process under study in such FIGS. For instance, FIG. 3A illustrates that as substrate temperature during deposition increases for a given deposition rate and film thickness (or deposition amount), the LSPR wavelength generally decreases. Furthermore, an increase in substrate temperature during deposition for a given deposition rate and film thickness generally results in smoothing of the resulting enhancement surface. FIG. 3B further illustrates that as deposition rate increases for a given substrate temperature and film thickness (or deposition amount), the LSPR wavelength generally increases. An increase in deposition rate for a given substrate temperature and film thickness generally results in roughening of the resulting enhancement surface. FIG. 3C also illustrates that as film thickness (or deposition amount) increases for a given substrate temperature and deposition rate, the LSPR wavelength generally increases. An increase in film thickness for a given substrate temperature and deposition rate generally results in roughening of the resulting enhancement surface. Accordingly, the deposition parameters of FIGS. 3A–3C support the view that as the enhancement surface is roughened, its LSPR wavelength generally increases. Thus, certain embodiments of the present invention enable deposition parameters to be controlled to tailor the roughness of the enhancement surface to effectively tune its LSPR wavelength to provide maximum extinction of a particular excitation light wavelength.

Through analysis (e.g., statistical analysis) of various deposition parameters and their interrelationship for a particular deposition process being utilized, a control equation may be derived to determine the proper deposition parameters to be used to produce a surface having a desired LSPR wavelength. For instance, in a preferred embodiment such a control equation includes deposition rate, substrate temperature during deposition, and deposition amount (or film thickness) as variables which may be controlled to produce an enhancement surface having a desired LSPR wavelength. Such a control equation may, for example, be coded within a software application, and such software application may be executed on a processor-based device (e.g., a personal computer) to generate the appropriate values of controlled deposition parameters that results in production of an enhancement surface having a desired LSPR wavelength (e.g., a LSPR wavelength that provides maximum extinction of a particular excitation light source applied thereto).

For example, in one implementation an equation having the following form may be derived:

$$\lambda_{LSPR} = \text{Coefficient}_1 + \text{Coefficient}_2 * T_S - \text{Coefficient}_3 * R_D - \text{Coefficient}_4 * T_f - \text{Coefficient}_5 * T_S^2 + \text{Coefficient}_6 * T_S * R_D - \text{Coefficient}_7 * T_S * T_f + \text{Coefficient}_8 * R_D^2 + \text{Coefficient}_9 * R_D * T_f + \text{Coefficient}_{10} * T_f^2$$

where $\lambda_{LSPR}$ is the desired LSPR wavelength in nanometers, $T_S$ is the substrate temperature during deposition, $R_D$ is the deposition rate, and $T_f$ is the film thickness. Through statistical analysis of a deposition process under study, appropriate values for the various coefficients of such equation (i.e., $\text{Coefficient}_1 - \text{Coefficient}_{10}$) may be determined.

As an example, in a specific implementation of a preferred embodiment (such implementation corresponds to the above description of FIGS. 1, 2, and 3A–3C), an analysis was conducted (as described in greater detail hereafter) of a thermal evaporation deposition process for depositing a silver film to derive the following equation:

$$\lambda_{LSPR} = 360.371 + 2.14467 * T_S - 423.025 * R_D - 0.525988 * T_f - 0.00110417 * T_S^2 + 0.0388889 * T_S * R_D - 0.0346889 * T_S * T_f + 118.313 * R_D^2 305.42963 * R_D * T_f + 0.0510658$$

where $\lambda_{LSPR}$ is the desired LSPR wavelength in nanometers (nm), $T_S$ is the substrate temperature during deposition (in °C.), RD is the deposition rate (in A/s), and $T_f$ is the film thickness in Å. From such an equation, the LSPR wavelength ($\lambda_{LSPR}$) can be determined for various values of $T_S$, $R_D$, and $T_f$. Alternatively, given a particular LSPR wavelength that is desired, suitable values of $T_S$, $R_D$, and $T_f$ that result in such particular LSPR wavelength can be determined using the above equation.

More specifically, an analysis was conducted by first producing various silver film samples through the thermal evaporation deposition process under study with one or more deposition parameters varied in each sample (such as the exemplary 17 samples of FIGS. 1 and 2). For instance, one or more of deposition rate, substrate temperature during deposition, and deposition amount (film thickness) were controllably varied in producing each sample. The resulting LSPR wavelength achieved for each resulting sample was recorded, along with the deposition parameter values used in producing such sample. Analysis is then performed to determined the effect that each deposition parameter has on the resulting LSPR wavelength. For instance, further samples may be produced by maintaining all but one of the deposition parameters constant, and varying one deposition parameter in each sample to evaluate the amount of effect that such one deposition parameter has on the resulting LSPR wavelength. The specific relationship observed for this example is charted in the above FIGS. 3A–3C, and is further described with FIGS. 4–7 hereafter. Through such analysis the above control equation was derived, which defines the relationship of deposition parameters $T_S$, $R_D$, and $T_f$ and particular coefficient values for the specific deposition process under study to enable determination of appropriate values for such deposition parameters that yield a desired LSPR wavelength ($\lambda_{LSPR}$). It should be understood that various other control equations may be derived in a similar manner for other specific deposition processes. Thus, the present invention is not intended to be limited to the exemplary control equation (s) described herein, but instead such control equation(s) and the derivation thereof are intended solely as examples which render the disclosure enabling for derivation of other control equations.

Figure 4:
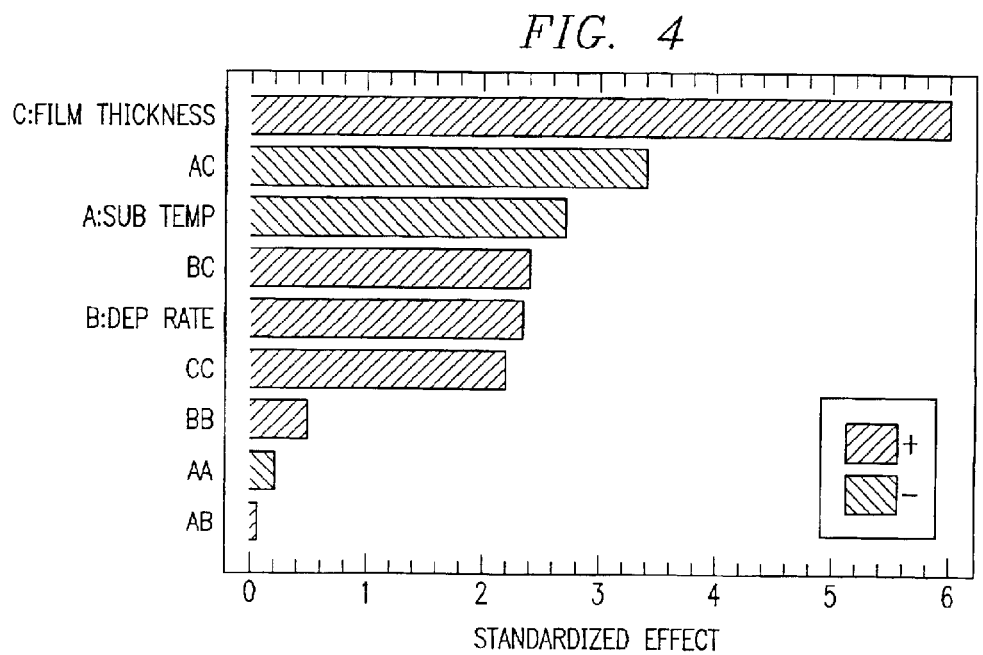
FIG. 4 shows a standardized Pareto Chart illustrating the relative effect that various controllable deposition parameters of a preferred embodiment have on the plasmon resonance wavelength of the resulting enhancement surface.

Turning to FIG. 4, a standardized Pareto Chart (chart that shows information in order of magnitude) is shown illustrating the effect that various deposition parameters have on the LSPR wavelength of a resulting enhancement surface produced by the exemplary deposition process for which the above-equation is derived (e.g., a particular thermal evaporation process utilized to deposit a silver film on a substrate). More specifically, FIG. 4 illustrates the influence on LSPR wavelength of the deposition parameters of a preferred embodiment, e.g., substrate temperature (also represented as parameter "A"), deposition rate (also represented as parameter "B"), and film thickness (also represented as parameter "C"), as well as the interrelation of such parameters. As shown, film thickness (or parameter "C") is the most influential on LSPR wavelength of the deposition parameters under study in FIG. 4. Accordingly, to accurately tailor the LSPR wavelength in a desired manner, it may be desirable to most accurately control the film thickness parameter, as such parameter has the greatest influence on the resulting LSPR wavelength. More specifically, in a preferred embodiment, a deposition process is utilized wherein the amount of film thickness (or deposition amount) is a tightly controlled parameter in producing an enhancement surface having a desired plasmon wavelength.

Each of the deposition parameters and interrelationships shown in the chart of FIG. 4 relate to a term in the derived equation:

$$\lambda_{LSPR}=360.371+2.14467*T_S-423.025*R_D-0.525988*T_f-0.00110417*T_S^2+0.0388889*T_S*R_D-0.0346889*T_S*T_f+118.313*R_D^2+5.42963*R_D*T_f+0.0510658*T_f^2$$

For instance, the film thickness parameter ("A") relates to the variable $T_f$ in such equation. Because film thickness has the greatest effect on the resulting LSPR wavelength (as shown in FIG. 4), it may be important to most accurately control the variable $T_f$, as well as its corresponding coefficient (i.e., the term $-0.525988*T_f$) in the above equation to produce a surface having a desired LSPR wavelength $\lambda_{LSPR}$. Specifically, each of the deposition parameters and interrelationships shown in the chart of FIG. 4 relate to a corresponding term in the above equation as shown in table 1 below:

TABLE 1

| Deposition Parameter from FIG. 4 | Corresponding Term of Derived Equation |
|---|---|
| C | $-0.525988*T_f$ |
| AC | $-0.0346889*T_S*T_f$ |
| A | $+2.14467*T_S$ |
| BC | $+5.42963*R_D*Tf$ |
| B | $-423.025*R_D$ |
| CC | $+0.0510658*T_f^2$ |
| BB | $+118.313*R_D^2$ |
| AA | $-0.00110417*T_S^2$ |
| AB | $+0.0388889*T_S*R_D$ |

From FIG. 4, it can be determined which of the corresponding terms of the derived equation have the greatest effect on the accuracy of the LSPR wavelength of a surface produced by a particular deposition process. As further shown in FIG. 4, the interrelation between substrate temperature and film thickness (shown as parameter "AC") is the second most influential on LSPR wavelength of the deposition parameters under study in FIG. 4. Such interrelationship has a relatively great effect on the resulting LSPR wavelength. Thus, to achieve a desired LSPR wavelength, if the substrate temperature is altered slightly from the temperature determined to be appropriate for producing the desired LSPR, the film thickness will likely need to be altered from the value determined to be appropriate for producing the desired LSPR in order to compensate for the change in substrate temperature to enable the desired LSPR wavelength to be produced. Such interrelationship of substrate temperature and film thickness (AC) relates to the term $T_S*T_f$ in the above equation. Because the interrelationship of substrate temperature and film thickness is determined to have such a great effect on the resulting LSPR wavelength, it may be important to accurately control the variables $T_S$ and $T_f$, as well as the corresponding coefficient of the term $-0.0346889*T_S*T_f$ in the above equation to produce a surface having a desired LSPR wavelength $\lambda_{LSPR}$.

Substrate temperature (shown as parameter "A") is the third most influential on LSPR wavelength of the deposition parameters under study in the example of FIG. 4. Substrate temperature (A) relates to the term $T_S$ in the above equation. Therefore, it may be important to accurately control the variable $T_S$, as well as its corresponding coefficient (i.e., the term $+2.14467*T_S$) in the above equation to produce a surface having a desired LSPR wavelength The fourth most influential parameter on LSPR wavelength is the interrelation between deposition rate and film thickness (shown as parameter "BC"). Such interrelationship illustrates that to achieve a desired LSPR wavelength, if the deposition rate is altered slightly from the deposition rate determined to be appropriate for producing the desired LSPR, the film thickness may need to be altered from the value determined to be appropriate for producing the desired LSPR in order to compensate for the change in deposition rate to enable the desired LSPR wavelength to be produced. Such interrelationship of deposition rate and film thickness (BC) relates to the term $R_D*T_f$ in the above equation. Thus, a process may be implemented that enables accurate control of the variables $R_D$ and $T_f$, as well as the corresponding coefficient of the term $+5.42963*R_D*T_f$ in the above equation to produce a surface having a desired LSPR wavelength $\lambda_{LSPR}$.

Deposition rate (shown as parameter "B") is the fifth most influential on LSPR wavelength of the deposition parameters under study in the example of FIG. 4. Deposition rate (B) relates to the term $R_D$ in the above equation. Therefore, it may be important to accurately control the variable $R_D$, as well as its corresponding coefficient (i.e., the term $-423.025*R_D$) in the above equation to produce a surface having a desired LSPR wavelength $\lambda_{LSPR}$.

The sixth most influential parameter on LSPR wavelength is shown as parameter "CC" in the example of FIG. 4, which corresponds to the film thickness squared term of the above equation (i.e., term $+0.0510658*T_f^2$). Therefore, it may be important to accurately control such term $+0.0510658*T_f^2$ of the above equation to produce a surface having a desired LSPR wavelength $\lambda_{LSPR}$.

As shown in the example of FIG. 4, the seventh most influential parameter on LSPR wavelength is parameter "BB," which has relatively much less influence on the resulting LSPR wavelength than the parameters listed above it. Parameter BB corresponds to the deposition rate squared term of the derived equation (i.e., term $+118.313*R_D^2$). Therefore, it may be somewhat important to accurately control such term $+118.313*R_D^2$ of the derived equation to produce a surface having a desired LSPR wavelength $\lambda_{LSPR}$. Additionally, the next most influential parameter on LSPR wavelength is shown as parameter "1" in the example of FIG. 4, which corresponds to the substrate temperature squared term of the derived equation (i.e., term $-0.00110417*T_S^2$). Therefore, it may be somewhat important to accurately control such term $-0.00110417*T_S^2$ of the derived equation to produce a surface having a desired LSPR wavelength $\lambda_{LSPR}$.

The least influential parameter on LSPR wavelength in the example of FIG. 4 is the interrelation between substrate temperature and deposition rate (shown as parameter "AB"). Such interrelationship illustrates that to achieve a desired LSPR wavelength, if the substrate temperature is altered slightly from the temperature determined to be appropriate for producing the desired LSPR, the deposition rate may not need to be altered to compensate for the change in substrate temperature, as the effect that such interrelation has on the resulting LSPR wavelength is relatively minor. Such interrelationship of substrate temperature and deposition rate (AB) relates to the term $+0.0388889*T_S*R_D$ in the derived equation. Thus, from FIG. 4, it may be determined that relatively little control is needed over such term $+0.0388889*T_S*R_D$. For instance, the derived equation may be varied by varying the coefficient $+0.0388889$ in such term without greatly effecting the accuracy of the derived equation. Further, the derived equation may even be altered by completely removing the term $+0.0388889*T_S*R_D$ therefrom, and the altered equation may still render a relatively accurate result in determining appropriate deposition parameters to be utilized in producing a metal surface having a desired LSPR wavelength because the removed term has been determined (from the analysis of FIG. 4) to have a relatively small effect on the resulting LSPR wavelength.

Accordingly, it may be desirable to ensure the greatest control over the deposition parameters having the greatest influence on the LSPR wavelength, and having great control over those deposition parameters having relatively little influence on the LSPR wavelength may therefore be unnecessary in certain embodiments. Thus, control over those parameters having relatively little influence on the LSPR wavelength may be relaxed in certain implementations. However, it may be desirable in certain embodiments to tightly control all of such deposition parameters to ensure great accuracy in the resulting LSPR wavelength.

Accordingly, various embodiments of the present invention enable an enhancement surface to be produced which has a desired LSPR wavelength (e.g., a LSPR wavelength that provides maximum exertion of a particular excitation light). As an example of application of a preferred embodiment, assume a user utilizes an Argon ion laser as the excitation light source within a surface-enhanced spectroscopy process (e.g., SERS), and further assume that such Argon ion laser is capable of emitting laser radiation at wavelengths of either 514.5 nm or 488.0 nm. Thus, the user desires an enhancement surface for use within the surface-enhanced spectroscopy (e.g., SERS) that provides optimum enhancement. More specifically, the user desires an enhancement surface for use within the surface-enhanced spectroscopy that provides a maximum plasmon resonance wavelength at either 514.5 nm or 488.0 nm to allow maximum extinction of the excitation light source.

According to various embodiments, deposition parameters may be controlled to produce an enhancement surface having a desired LSPR wavelength (e.g., a LSPR wavelength of either 514.5 nm or 488.0 nm in this example). For instance, utilizing the above-described derived equation of one implementation of a preferred embodiment, suitable values for substrate temperature, deposition rate, and film thickness (or deposition amount) to be used in the deposition process may be accurately determined for producing an enhancement surface having the desired LSPR wavelength. For example, to produce a silver (Ag) film having a LSPR wavelength of 514.5 nm, the above equation may be utilized to determine that the parameter values as provided in Table 2 are suitable for producing such a silver film.

TABLE 2

| Substrate Temperature (° C.) | Deposition Rate (Å/s) | Film Thickness (Å) |
|---|---|---|
| 260 | 0.3 | 120 |
| 195 | 0.6 | 75 |
| 220 | 0.3 | 30 |

Thus, a silver enhancement surface having a LSPR wavelength of 514.5 nm can be produced by utilizing any one of the three options for deposition parameter values provided in Table 2. That is, performing deposition of the silver film on a clean, smooth substrate that has temperature 260° C. at a deposition rate of 0.3 Å per second (Å/s), to form a film thickness of 120 Å will result in a silver enhancement surface having the desired 514.5 nm LSPR wavelength. Alternatively, performing deposition of the silver film on a clean, smooth substrate that has temperature 195° C., at a deposition rate of 0.6 Å/s, to form a film thickness of 75 Å will result in a silver enhancement surface having the desired 514.5 nm LSPR wavelength. As a further alternative, performing deposition of the silver film on a clean, smooth substrate that has temperature 220° C., at a deposition rate of 0.3 Å/s, to form a film thickness of 30 Å will result in a silver enhancement surface having the desired 514.5 nm LSPR wavelength. Thus, any of the various silver films (e.g., having different thickness) may be produced according to the above deposition parameters to satisfy the user's desire for an enhancement surface that has a LSPR wavelength of 514.5 nm.

As another example, to produce a silver (Ag) film having a LSPR wavelength of 488.0 nm, the above equation may be utilized to determine that the parameter values as provided in Table 3 are suitable for producing such a silver film.

TABLE 3

| Substrate Temperature (° C.) | Deposition Rate (Å/s) | Film Thickness (Å) |
|---|---|---|
| 290 | 0.45 | 120 |
| 200 | 0.4 | 75 |
| 180 | 0.3 | 30 |

Thus, a silver enhancement surface having an LSPR wavelength of 488 nm can be produced by utilizing any one of the three options for deposition parameter values provided in Table 3. That is, performing deposition of the silver film on a clean, smooth substrate that has temperature 290° C., at a deposition rate of 0.45 Å/s, to form a film thickness of 120 Å will result in a silver enhancement surface having the desired 488 nm LSPR wavelength. Alternatively, performing deposition of the silver film on a clean, smooth substrate that has temperature 200° C., at a deposition rate of 0.4 Å's, to form a film thickness of 75 Å will result in a silver enhancement surface having the desired 488 nm LSPR wavelength. As a further alternative, performing deposition of the silver film on a clean, smooth substrate that has temperature 180° C., at a deposition rate of 0.3 Å/s, to form a film thickness of 30 Å will result in a silver enhancement surface having the desired 488 nm LSPR wavelength. Thus, any of the various silver films (e.g., having different thickness) may be produced according to the above deposition parameters to satisfy the user's desire for an enhancement surface that has a LSPR wavelength of 488 nm.

Figure 5:
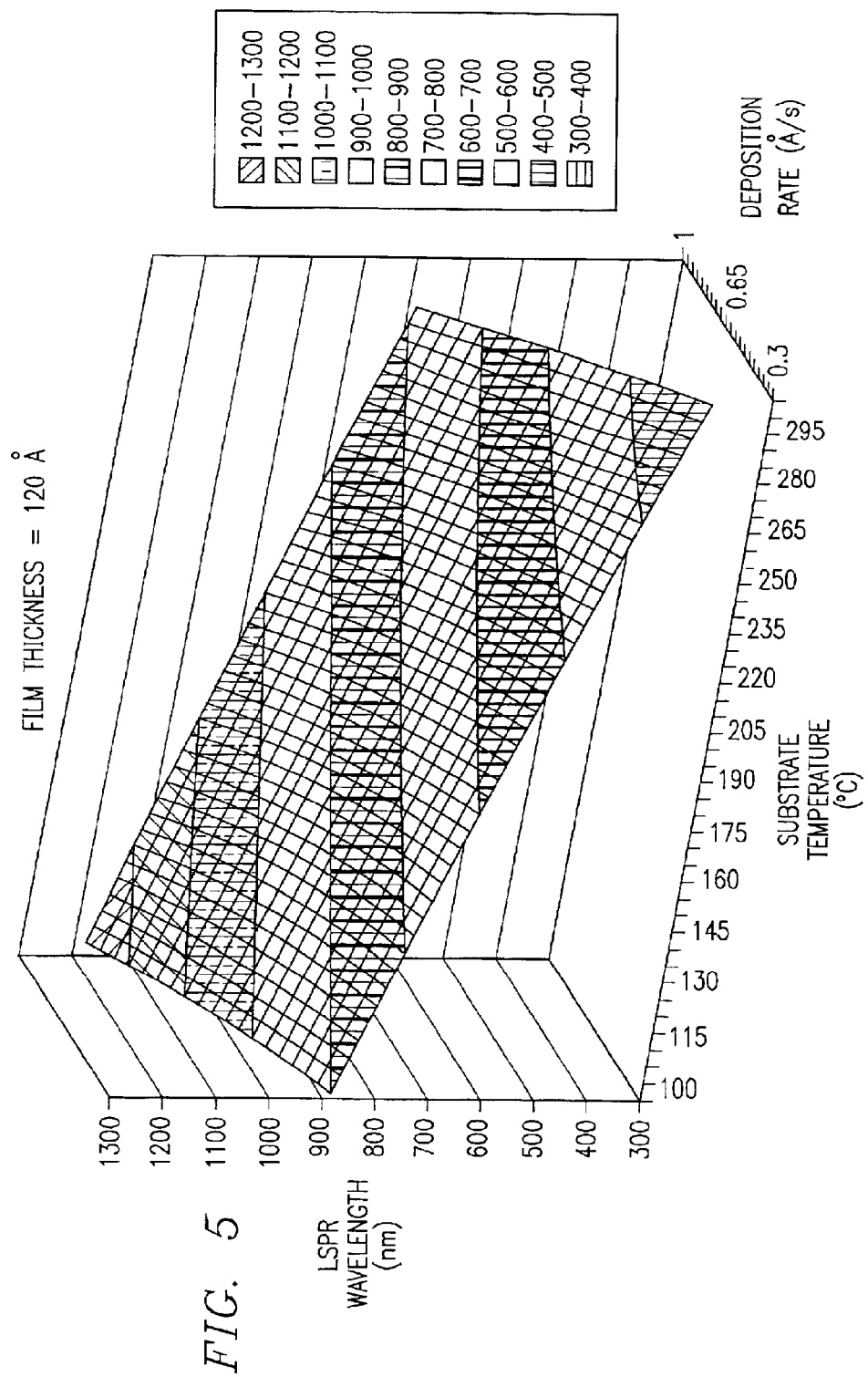
FIG. 5 shows an exemplary plot illustrating the resulting plasmon resonance wavelengths that can be generated over various controllable deposition parameter values, in which the film thickness deposition parameter is fixed at 120 Å.

Furthermore, it should be understood that a preferred embodiment provides a relatively stable solution. For instance, turning to FIG. 5, an exemplary plot is shown illustrating the resulting LSPR wavelengths that can be generated over various controllable deposition parameter values according to the above-described deposition process (e.g., utilizing the deposition process for which the above-described equation is derived), in which the film thickness deposition parameter is fixed at 120 Å. As the plot of FIG. 5 illustrates, in a preferred embodiment the variability of substrate temperature and deposition rate is relatively small and LSPR insensitive. As FIG. 5 illustrates, the deposition parameters are very monotonic, and therefore are very much under control. That is, substrate temperature and deposition rate are very monotonic, which enables relatively relaxed control of the deposition process in producing the desire LSPR wavelength. For instance, the slope of the resulting plot of LSPR wavelengths in FIG. 5 is relatively gradual, thereby indicating that when film thickness is set to 120 Å control of the substrate temperature and deposition rate may be relatively relaxed while enabling a desired LSPR wavelength to be accurately achieved.

Continuing with the example described above in conjunction with Table 2 wherein a silver film having a LSPR wavelength of 514.5 nm is desired, from the derived equation for a particular deposition process it is determined that one option of deposition parameters that may be utilized to produce such a desired silver film is film thickness 120 Å, deposition rate 0.3 Å/s, and substrate temperature 260° C. The plot of FIG. 5 illustrates that if film thickness is accurately controlled to 120 Å, then slight variances in the deposition rate and substrate temperature from the determined values of 0.3 Å/s and 260° C. may still provide relatively accurate control over the resulting LSPR wavelength (i.e., to achieve approximately 514.5 nm wavelength). That is, as shown in FIG. 5, slight variances in substrate temperature and deposition rate for film thickness 120 Å result in only a slight variance in the resulting LSPR wavelength.

Figure 6:
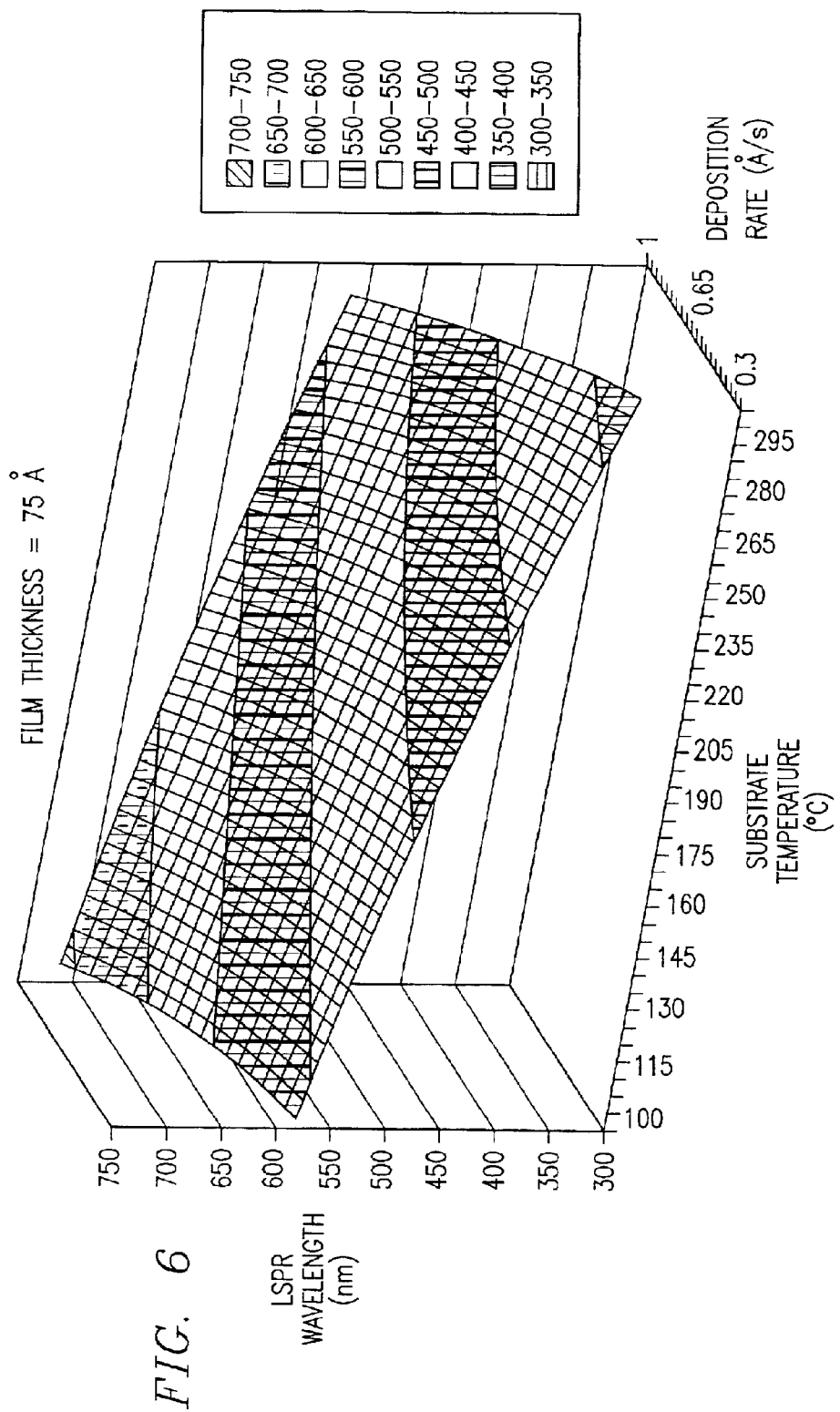
FIG. 6 shows an exemplary plot illustrating the resulting plasmon resonance wavelengths that can be generated over various controllable deposition parameter values, in which the film thickness deposition parameter is fixed at 75 Å.

FIG. 6 shows a further exemplary plot illustrating the resulting LSPR wavelengths that can be generated over various controllable deposition parameter values according to the above-described deposition process of a preferred embodiment, in which the film thickness deposition parameter is fixed at 75 Å. That is, FIG. 6 provides further analysis of the stability of the solution derived for a particular deposition process. As the plot of FIG. 6 illustrates, in a preferred embodiment the variability of substrate temperature and deposition rate is relatively small and LSPR insensitive when the film thickness is set to 75 Å. As FIG. 6 illustrates, the deposition parameters are very monotonic, and therefore are very much under control. That is, substrate temperature and deposition rate are very monotonic, which enables relatively relaxed control of the deposition process in producing the desire LSPR wavelength. For instance, the slope of the resulting plot of LSPR wavelengths in FIG. 6 is relatively gradual, thereby indicating that when film thickness is set to 75 Å, control of the substrate temperature and deposition rate may be relatively relaxed while enabling a desired LSPR wavelength to be accurately achieved.

Continuing with the example described above in conjunction with Table 2 wherein a silver film having a LSPR wavelength of 514.5 nm is desired, from the derived equation for a particular deposition process it is determined that one option of deposition parameters that may be utilized to produce such a desired silver film is film thickness 75 Å, deposition rate 0.6 Å/s, and substrate temperature 195° C. The plot of FIG. 6 illustrates that if film thickness is accurately controlled to 75 Å, then slight variances in the deposition rate and substrate temperature from the determined values of 0.6 Å's and 195° C. may still provide relatively accurate control over the resulting LSPR wavelength (i.e., to achieve approximately 514.5 nm wavelength). That is, as shown in FIG. 6, slight variances in substrate temperature and deposition rate for film thickness 75 Å result in only a slight variance in the resulting LSPR wavelength.

Figure 7:
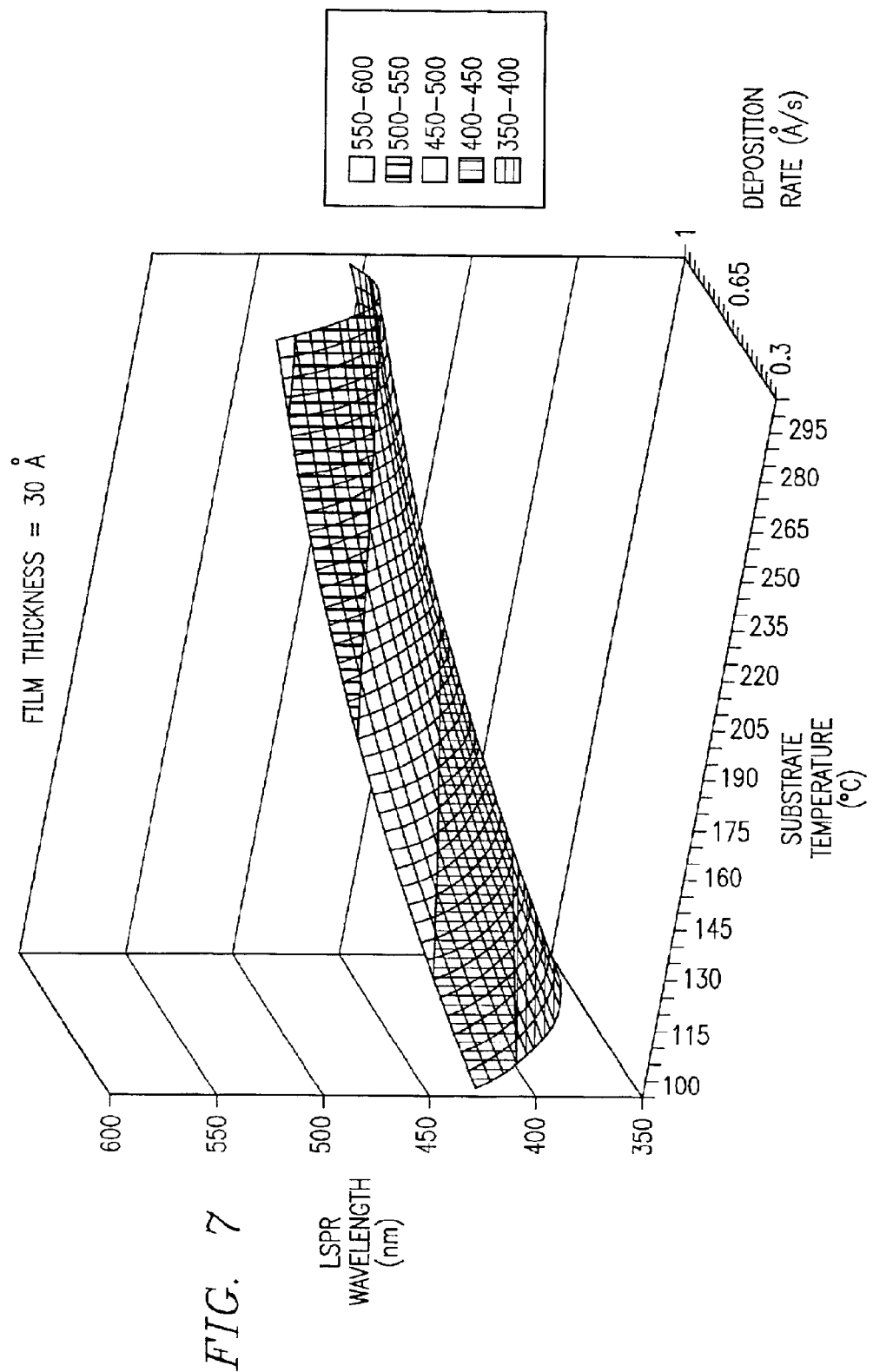
FIG. 7 shows an exemplary plot illustrating the resulting plasmon resonance wavelengths that can be generated over various controllable deposition parameter values, in which the film thickness deposition parameter is fixed at 30 Å.

FIG. 7 shows a further exemplary plot illustrating the resulting LSPR wavelengths that can be generated over various controllable deposition parameter values according to the above-described deposition process of a preferred embodiment, in which the film thickness deposition parameter is fixed at 30 Å. That is, FIG. 7 provides further analysis of the stability of the solution derived for a particular deposition process. As the plot of FIG. 7 illustrates, in a preferred embodiment the variability of substrate temperature and deposition rate is relatively small and LSPR insensitive when the film thickness is set to 30 Å. As FIG. 7 illustrates, the deposition parameters are very monotonic, and therefore are very much under control. That is, substrate temperature and deposition rate are very monotonic, which enables relatively relaxed control of the deposition process in producing the desire LSPR wavelength. For instance, the slope of the resulting plot of LSPR wavelengths in FIG. 7 is relatively gradual, thereby indicating that when film thickness is set to 30 Å, control of the substrate temperature and deposition rate may be relatively relaxed while enabling a desired LSPR wavelength to be accurately achieved.

Continuing with the example described above in conjunction with Table 2 wherein a silver film having a LSPR wavelength of 514.5 nm is desired, from the derived equation for a particular deposition process it is determined that one option of deposition parameters that may be utilized to produce such a desired silver film is film thickness 30 Å, deposition rate 0.3 Å/s, and substrate temperature 220° C. The plot of FIG. 7 illustrates that if film thickness is accurately controlled to 30 Å, then slight variances in the deposition rate and substrate temperature from the determined values of 0.3 Å/s and 220° C. may still provide relatively accurate control over the resulting LSPR wavelength (i.e., to achieve approximately 514.5 nm wavelength). That is, as shown in FIG. 7, slight variances in substrate temperature and deposition rate for film thickness 30 Å result in only a slight variance in the resulting LSPR wavelength.

As FIGS. 5–7 illustrate, the deposition parameters are very monotonic, and therefore are very much under control. That is, substrate temperature and deposition rate are very monotonic, which enables relatively relaxed control of the deposition process in producing the desire LSPR wavelength. Thus, in this manner, the stability of the derived solution for a particular deposition process may be analyzed over different deposition parameters.

In view of the above, various embodiments of the present invention provide a technique for producing an enhancement surface that has a LSPR wavelength accurately tuned to a desired value (e.g., to the value that provides maximum extinction of an excitation light source directed toward such enhancement surface). Recent attempts to provide a tunable LSPR wavelength of an enhancement surface have been made in the prior art. One suggestion has been advanced by Richard P. Van Duyne, et al. in an article titled "Nanosphere Lithography: Tunable Localized Surface Plasmon Resonance Spectra of Silver Nanoparticles," *J. Phys. Chem.* B 2000, 104, 10549–10556. Van Duyne suggests a technique of producing a silver film wherein a 2D colloidal crystal mask is first formed on a clean substrate, then the silver film is deposited over the mask, and the mask is then removed by sonicating the entire substrate in either $CH_2Cl_2$ or absolute ethanol, thereby resulting in an array of triangularly shaped silver particles remaining on the substrate.

While Van Duyne suggests the ability to tune throughout the visible and into the IR spectrum by changing either (1) the out-of-plane height of the silver particles, (2) the in-plane width of the silver particles, or (3) the shape of the individual silver particles, it is unclear exactly how to change such features to produce a particular LSPR wavelength. Further, such technique requires first applying a mask to a substrate surface and then later removing such mask to produce the arrangement of silver particles. Accordingly, certain embodiments of the present invention provide a much simpler technique of producing an enhancement surface having a desired LSPR wavelength in that the metal (e.g., silver) may be deposited directly on a clean, smooth substrate without requiring use of a mask. Further, it appears that various embodiments of the present invention enable a desired LSPR wavelength to be achieved at least as accurately as with the technique suggested by Van Duyne. Another suggestion has been advanced by W. Gotschy, et al. in an article titled "Thin films by regular patterns of metal nanoparticles: tailoring the optical properties by nanodesign," *Appl. Phys.* B 63, 381–384 (1996). Gotschy teaches utilizing an electron-beam lithography procedure to produce a silver film. More specifically, Gotschy suggests a technique of producing: a silver film wherein a Polymethyl-Metacrylate (PMMA) plymere layer (e.g., PMMA "mask") is first formed on a clean substrate, then the silver film is deposited over such PMMA mask via thermal evaporation process, and the mask (along with the portion of the silver resting on top of such PMMA layer) is then removed by acetone in a lift-off process, thereby resulting in an array of silver nanoparticles remaining on the substrate.

As with Van Duyne's technique, Gotschy's technique requires first applying a mask to a substrate surface and then later removing such mask to produce the array of silver particles. Accordingly, certain embodiments of the present invention provide a much simpler technique of producing an enhancement surface having a desired LSPR in that the metal (e.g., silver) may be deposited directly on a clean, smooth substrate without requiring use of a mask. Further, Gotschy fails to teach such control over the LSPR wavelength that may be achieved by various embodiments of the present invention. For instance, Gotschy illustrates a plot showing the extinction amount over a range of wavelengths (see FIG. 1 of Gotschy). The graph illustrates that such extinction plots have a curve with a very gradual slope over such range of wavelengths, as opposed to the exemplary extinction plots provided in FIG. 2 herein, which provide much steeper slopes. Accordingly, various embodiments of the present invention enable LSPR wavelength to be accurately tuned to any desired wavelength, as opposed to the limited wavelengths taught in Gotschy, thereby providing much greater flexibility.

It should be understood that while an exemplary implementation of a preferred embodiment is described above for producing a silver (Ag) surface having a desired LSPR wavelength, various embodiments of the present invention may be implemented for producing any other metal surface capable of being deposited by thermal evaporation (or other deposition process), including without limitation gold (Au) and copper (Cu).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of producing a metal surface having a desired localized surface plasmon resonance wavelength, comprising the steps of:

depositing metal onto a substrate that does not have a mask prearranged thereon; and controlling one or more deposition parameters of said depositing step to tailor the localized surface plasmon resonance of said metal to a desired wavelength.

2. The method of claim 1 wherein said one or more deposition parameters include at least one of the parameters selected from the group consisting of:

temperature of said substrate during said depositing step, deposition rate, and amount of said metal deposited during said depositing step.

3. The method of claim 1 wherein said controlling step includes controlling each of the following deposition parameters:

temperature of said substrate during said depositing step, deposition rate, and amount of said metal deposited during said depositing step.

4. The method of claim 1 wherein said metal is selected from the group consisting of: silver, gold, and copper.

5. The method of claim 1 further comprising the step of: utilizing a thermal evaporator to perform said depositing step.

6. The method of claim 1 further comprising the step of utilizing any of the following to perform said depositing step:

thermal evaporation, sputter deposition, electron-beam lithography, laser ablation, and chemical vapor deposition.

7. The method of claim 1 further comprising the step of: determining said desired wavelength.

8. The method of claim 7 wherein said desired wavelength is a wavelength that provides maximum extinction of a particular excitation light source.

9. The method of claim 1 further comprising the step of: determining at least one appropriate value for each of said one or more deposition parameters that result in said localized surface plasmon resonance of said metal having said desired wavelength.

10. The method of claim 9 further comprising the step of: utilizing a control algorithm to perform said determining step.

11. The method of claim 10 further comprising the step of:
deriving said control algorithm through analysis of a particular deposition process utilized to perform said depositing step.

12. A method of producing an enhancement surface for use in a surface-enhanced spectroscopy process, wherein said enhancement surface has a desired localized surface plasmon resonance wavelength, said method comprising the steps of:
determining the wavelength of an excitation light source used in said surface-enhanced spectroscopy process;
determining an appropriate value for one or more deposition parameters to use in depositing metal onto a substrate to produce an enhancement surface having a localized surface plasmon resonance wavelength that provides optimum enhancement for said excitation light source; and
depositing metal onto a substrate in accordance with the determined value for one or more deposition parameters to produce an enhancement surface having said localized surface plasmon resonance wavelength that provides optimum enhancement for said excitation light source, wherein said substrate does not have a mask prearranged thereon.

13. The method of claim 12 wherein said one or more deposition parameters include at least one of the parameters selected from the group consisting of:
temperature of said substrate during said depositing step, deposition rate, and amount of said metal deposited during said depositing step.

14. The method of claim 12 wherein said step of determining an appropriate value one or more deposition parameters includes determining an appropriate value for each of the following deposition parameters:
temperature of said substrate during said depositing step, deposition rate, and amount of said metal deposited during said depositing step.

15. The method of claim 12 wherein said metal is selected from the group consisting of: silver, gold, and copper.

16. The method of claim 12 further comprising the step of:
utilizing a thermal evaporator to perform said depositing step.

17. The method of claim 12 further comprising the step of utilizing any of the following to perform said depositing step:
thermal evaporation, sputter deposition, electron-beam lithography, laser ablation, and chemical vapor deposition.

18. The method of claim 12 wherein said excitation light source is a laser.

19. The method of claim 12 wherein said localized surface plasmon resonance wavelength that provides optimum enhancement comprises:
a wavelength that provides maximum extinction of said excitation light source.

20. The method of claim 12 wherein said step of determining an appropriate value for one or more deposition parameters further comprises the step of:
utilizing a control algorithm to perform said determining of said appropriate value for one or more deposition parameters.

21. The method of claim 20 further comprising the step of:
deriving said control algorithm through analysis of a particular deposition process utilized to perform said depositing step.

22. The method of claim 12 wherein said surface-enhanced spectroscopy process includes surface-enhanced Raman spectroscopy.

23. A method of producing a metal film having a desired localized surface plasmon resonance wavelength, said method comprising the steps of:
determining appropriate values for deposition parameters to use in depositing metal onto a substrate to produce a metal film having a localized surface plasmon resonance LSPR of a desired wavelength, wherein said deposition parameters include deposition rate, substrate temperature, and thickness of said metal film; and
depositing said metal onto said substrate in accordance with the determined deposition parameter values to produce a metal film having said localized surface plasmon resonance of a desired wavelength.

24. The method of claim 23 wherein said metal is selected from the group consisting of: silver, gold, and copper.

25. The method of claim 23 further comprising the step of:
utilizing a thermal evaporator to perform said depositing step.

26. The method of claim 23 further comprising the step of utilizing any of the following to perform said depositing step:
thermal evaporation, sputter deposition, electron-beam lithography, laser ablation, and chemical vapor deposition.

27. The method of claim 23 further comprising the step of:
determining said desired wavelength of said localized surface plasmon resonance.

28. The method of claim 27 wherein said desired wavelength is a wavelength that provides maximum extinction of a particular excitation light source.

29. The method of claim 28 wherein said particular excitation light source includes a laser utilized in a surface-enhanced spectroscopy process.

30. The method of claim 23 further comprising the step of:
utilizing a control algorithm to perform said determining step.

31. The method of claim 30 further comprising the step of:
deriving said control algorithm through analysis of a particular deposition process utilized to perform said depositing step.

32. The method of claim 23 wherein said substrate does not include a mask prearranged thereon before said depositing step.

33. The method of claim 23 wherein said substrate is a smooth substrate.

34. The method of claim 23 comprising the step of:
cleaning said substrate before said depositing step, wherein no further pretreatment of said substrate is performed before said depositing step.

35. A method of deriving a control algorithm for controlling a deposition process in a manner that results in said deposition process producing a metal film that has a localized surface plasmon resonance of a desired wavelength, said method comprising:
utilizing a deposition process to deposit metal samples onto one or more substrates;
varying the value of at least one deposition parameter for each of said metal samples deposited;
analyzing said metal samples to determine the effect of said at least one deposition parameter on the localized surface plasmon resonance wavelength of said metal samples; and based on said analyzing step, determining said control algorithm that defines a resulting localized surface plasmon resonance wavelength of a metal film produced by said deposition process as a function of said at least one deposition parameter.

36. The method of claim 35 wherein one or more appropriate values of said at least one deposition parameter that results in production of a metal film having a localized surface plasmon resonance of a desired wavelength are determinable from said control algorithm.

37. The method of claim 36 wherein said desired wavelength is a wavelength that provides maximum extinction of a particular excitation light source.

38. The method of claim 35 wherein said at least one deposition parameter includes one or more of the parameters selected from the group consisting of:
   temperature of a substrate on which a metal is deposited by said deposition process to produce said metal film, deposition rate of said metal by said deposition process, and amount of said metal deposited by said deposition process.

39. The method of claim 35 wherein said at least one deposition parameter includes at least the following deposition parameters:
   temperature of a substrate on which a metal is deposited by said deposition process to produce said metal film, deposition rate of said metal by said deposition process, and amount of said metal deposited by said deposition process.

40. The method of claim 35 wherein said metal is selected from the group consisting of: silver, gold, and copper.

41. The method of claim 35 wherein said deposition process includes utilizing a thermal evaporator.

42. The method of claim 35 further comprising:
   coding said control algorithm into software code executable by a processor-based device.

43. The method of claim 42 wherein said software code is executable by said processor-based device to determine one or more appropriate values of said at least one deposition parameter that results in production of a metal film having a localized surface plasmon resonance of a desired wavelength.

* * * * *

UNITED STATES PATENT AND TRADEMARK OFFICE
CERTIFICATE OF CORRECTION

PATENT NO. : 6,838,121 B2 Page 1 of 1
DATED : January 4, 2005
INVENTOR(S) : Wayne A. Weimer It is certified that error appears in the above-identified patent and that said Letters Patent is hereby corrected as shown below:

<u>Column 15,</u>
Line 45, the word "exertion" should be -- extinction --.

Signed and Sealed this

Fifth Day of April, 2005

JON W. DUDAS
*Director of the United States Patent and Trademark Office*